Figure 1:
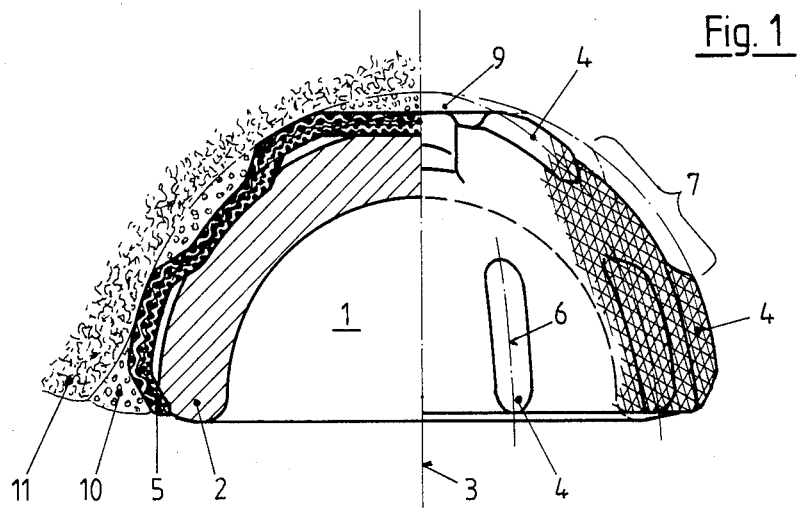

United States Patent [19]

Muller

[11] Patent Number: 4,813,960
[45] Date of Patent: Mar. 21, 1989

[54] ENDOPROSTHESIS FOR A HIP JOINT SOCKET

[75] Inventor: Maurice E. Muller, Bern, Switzerland

[73] Assignees: Sulzer Brothers Ltd., Winterthur; Protek AG, Bern, both of Switzerland

[21] Appl. No.: 11,130

[22] Filed: Feb. 5, 1987

[30] Foreign Application Priority Data

Feb. 18, 1986 [CH] Switzerland .................... 652/86

[51] Int. Cl.⁴ .................................. A61F 2/34
[52] U.S. Cl. ................................... 623/22
[58] Field of Search ............ 623/16, 18, 22, 23

[56] References Cited

U.S. PATENT DOCUMENTS 3,528,109  9/1970  Scales ........................ 623/22
4,479,271  10/1984  Bolesky et al. ........... 623/18
4,566,138  1/1986  Lewis et al. ............... 623/22

FOREIGN PATENT DOCUMENTS 0038902  11/1981  European Pat. Off. ....... 623/22
1506594  11/1967  France ............................. 623/22

Primary Examiner—Richard J. Apley
Assistant Examiner—David J. Isabella
Attorney, Agent, or Firm—Kenyon & Kenyon

[57] ABSTRACT

The hip joint endoprosthesis has a plastic socket body with a hemispherical outer surface and a wire mesh metal grid partially embedded in the socket body surface. The metal grid has a plurality of rib-like projections extending outwardly along meridian lines of the socket body in order to define regions therebetween for receiving a minimum thickness of bone cement for anchoring of the endoprosthesis in a bone.

9 Claims, 1 Drawing Sheet

ENDOPROSTHESIS FOR A HIP JOINT SOCKET

This invention relates to an endoprosthesis for a hip joint socket.

Heretofore, various types of endoprosthesis have been known for use as hip joint sockets. In some cases, the endoprostheses have been constructed for cement-free implantation while in other cases, the endoprostheses have been constructed for anchorage in a bone cement bed. In the latter cases, it has also been known to stiffen the endoprostheses made of plastic by "coating" the outer face with a multi-layer metal grid or wire mesh. Usually, these grids have one layer embedded in the plastic of the endoprosthesis for intimate connection of the plastic and metal while the remaining layers are intended to receive ingrowing bone tissue.

Generally, where an endoprosthesis having a metal grid on the exterior is pressed into a bone cement bed, the bone cement which is not yet hardened at the time of implantation will penetrate, on the one hand, into the "free pores" of the metal grid and, on the other hand, into the spongious bone tissue of the pelvis due to the pressure exerted on pressing in of the endoprosthesis. As is known, the bone cement is not an adhesive with adhesion effect. Instead, the anchoring forces are produced solely by a mechanical "hooking" of the cement to the mesh of the endoprosthesis as well as into the pores of the bone tissue. Thus, practice has shown that anchorage of a hip joint socket prosthesis with a metal grid is not sufficient if the spongiosa and metal grid "layers" permeated by the bone cement lie directly one on the other. That is, good adhesion requires a certain minimum depth of bone cement bed at least on portions of the outer skin of the socket. In the previously known sockets, which are generally structureless except for the lattice structure of the metal grid, the minimum thickness of a cement bed between the implant and bone is not ensured since the bone cement is pushed out of the surgical opening more or less in an uncontrollable manner as the socket is being pressed into the opening.

Accordingly, it is an object of the invention to ensure a required minimum thickness of bone cement bed at least in partial regions of an outer surface of a hip joint socket.

It is another object of the invention to provide a relatively simple surface structure for a hip joint socket for establishing a minimum thickness of bone cement bed between the socket and a bone.

Briefly, the invention provides an endoprosthesis for a hip joint socket which is comprised of an inner plastic socket body having a hemispherical outer surface and a multi-layer metal grid fixed to the surface with a plurality of uniformly distributed rib-like projections extending outwardly from the grid along meridian lines of the socket body.

The rib-like projections are spaced apart so as to define regions therebetween for receiving a minimum thickness of bone cement bed.

When the endoprosthesis is to be implanted into a bone, such as the pelvis, a bone cement bed is first placed within the surgically prepared opening of the bone. Next, the endoprosthesis is pressed into the bone cement bed to be anchored thereby. At this time, some of the bone cement penetrates into the spongiosa of the bone. Thereafter, the endoprosthesis is pressed into the bone cement bed so that the bone cement also penetrates into the pores of the metal grid. Because of the projections on the metal grid, even if the bone cement penetrates into the grid and into the spongiosa at the projections, or is displaced to the extent that the projections abut on the bone, a minimum thickness of the bone cement is preserved in the regions between the projections. Thus, the regions between the projections form catch basins for the bone cement which is displaced from the projections. The projections and the bone cement lying between the projections further constitute a safety device to prevent unintended rotation of the socket body within the bone cement bed.

One optimum pattern for providing a sufficient partial surface with a required minimum thickness of bone cement and for an optimum and uniform transmission of force has the projections of the metal grid offset to each other on opposite sides of a projection-free region in the middle latitudes of the socket body, i.e. in the medial region. In addition, the projections extend to a polar region of the grid without extending into the polar region so that the polar region is countersunk relative to the projections.

Figure 2:
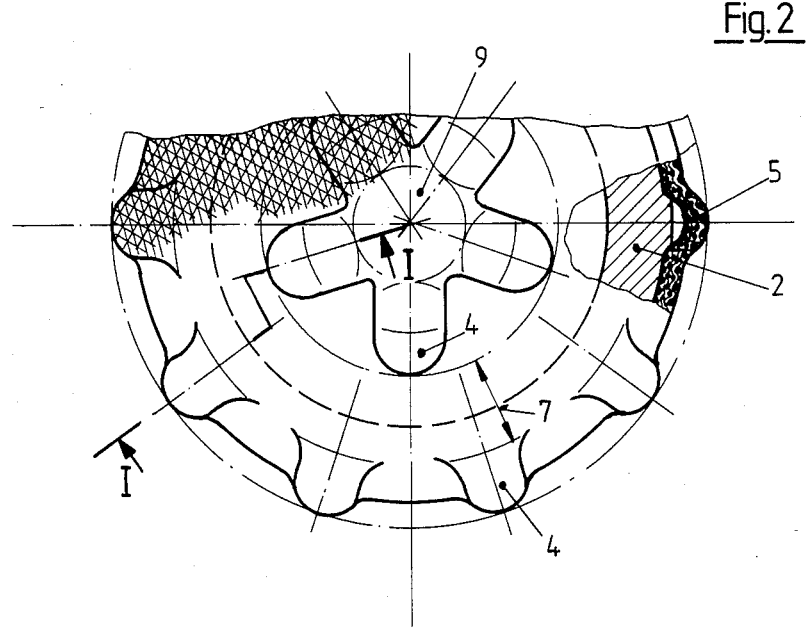

These and other objects and advantages of the invention will become more apparent from the following detailed description taken in conjunction with the accompanying drawings wherein:

FIG. 1 illustrates a cross sectional view taken on line I—I of FIG. 2 of an endoprosthesis constructed in accordance with the invention; and FIG. 2 illustrates a view taken at the polar region of the endoprosthesis of FIG. 1.

Referring to FIGS. 1 and 2, the endoprosthesis is constructed for use as a hip joint socket. To this end, the endoprosthesis has a hemispherical socket shell 1 for receiving a joint head (not shown) of a femur prosthesis and a socket body 2 of plastic, for example of polyethylene. In this respect, the socket shell 1 and socket body 2 are rotation-symmetrical to the socket axis 3 such that the socket body 2 has a hemispherical outer surface.

In addition, the endoprosthesis has a multi-layer wire mesh metal grid 5 fixed to the outer surface of the socket body 2. This grid serves as a reinforcing element while also serving to anchor the socket body 2 in a pelvis. In this regard, the metal grid 5 is partially embedded in the surface of the socket body 2 to the extent that the innermost layer of the grid 5 is at least partially embedded within the plastic of the socket body 2.

Referring to FIGS. 1 and 2, the metal grid 5 is provided with a plurality of uniformly distributed rib-like projections or beads 4 which extend outwardly along meridian lines 6 of the hemispherical outer surface of the socket body 2. These projections 4 are produced by mechanical deformation of the metal grid 5 before the plastic socket body 2 is pressed into the grid 5.

As indicated, the projections 4 are disposed in two circumferential rows with a projection-free zone 7 therebetween. As indicated in FIG. 1, the projection-free zone is disposed medially, i.e. in the middle geographic latitudes of the outer surface of the socket body 2. The projections 4 are sized to project from either side of the medial region 7 while also being arranged in offset manner with respect to each other. Further, the upper row of projections 4 extend to a polar region 9 of the metal grid 5 such that the polar region 9 is countersunk relative to the projections 4. In this respect, the polar region 9 of the metal grid 5 is undisturbed.

Because of the raised projections 4, when the endoprosthesis is pressed into a bone cement bed 10 within a spongious bone 11 (see FIG. 1) the projections 4 come into contact with the bone 11 while the regions between the projections 4 receive the bone cement. Thus, as indicated in FIG. 2, the relatively large area regions between the projections receive a sufficiently deep bone cement bed 10 to effect anchorage of the endoprosthesis in the bone 11.

The invention thus provides an endoprosthesis for a hip joint socket which is able to maintain a minimum of depth of bone cement between the "outer skin" of the endoprosthesis and the bone into which the endoprosthesis is implanted.

The minimum of depth of the bone cement bed—and therewith the minimum of the amount of projection of the ribs 4—should be 1 mm (milimeter) at least; preferably these depths or amounts respectively are 2 to 3 millimeters.

The range of thickness of the metal grid 5, for example, is 0.5 to 2 millimeters whereby the grid 5 generally consists of two or, at most, three layers.

What is claimed is:

1. An endoprosthesis for a hip joint socket comprising an inner plastic socket body having a hemispherical outer surface; and
a multi-layer metal grid fixed to said surface of said body, said grid forming a plurality of uniformly distributed rib-like projections extending outwardly along meridian lines for contacting bone while defining regions therebetween to receive bone cement, said projections being disposed on opposite sides of a rib-free region medially of said surface and in offset relation to each other.

2. An endoprosthesis as set forth in claim 1 wherein said grid is countersunk in a polar region relative to said projections.

3. An endoprosthesis as set forth in claim 2 wherein said grid is partially embedded in said body to at least partially fill said projections.

4. An endoprosthesis as set forth in claim 1 wherein said grid is partially embedded in said body to at least partially fill said projections.

5. An endoprosthesis for a hip joint socket comprising
a plastic socket body having a hemispherical outer surface; and
a wire mesh metal grid partially embedded in said surface of said plastic body, said grid forming a plurality of rib-like projections extending outwardly thereof for contacting bone while defining regions therebetween to receive a bone cement bed said projections being disposed along meridian lines of said hemispherical surface.

6. An endoprosthesis as set forth in claim 5 wherein said projections are disposed in two circumferential rows with a projection-free zone therebetween.

7. An endoprosthesis as set forth in claim 5 wherein said projections extend to a polar region of said grid whereby said polar region is countersunk relative to said projections.

8. An endoprosthesis as set forth in claim 5 wherein said projections are uniformly distributed over said socket surface.

9. An endoprosthesis as set forth in claim 5 wherein said grid is of multi-layer construction.

* * * * *